(12) United States Patent
Hilpert et al.

(10) Patent No.: US 8,815,841 B2
(45) Date of Patent: Aug. 26, 2014

(54) 1,4-OXAZEPINES AS BACE1 AND/OR BACE2 INHIBITORS

(75) Inventors: Hans Hilpert, Muenchenstein (CH); Robert Narquizian, Zaessingue (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 7 days.

(21) Appl. No.: 13/369,322

(22) Filed: Feb. 9, 2012

(65) Prior Publication Data
US 2013/0040936 A1    Feb. 14, 2013

(30) Foreign Application Priority Data
Feb. 18, 2011    (EP) .................................... 11155051

(51) Int. Cl.
*A61K 31/553*    (2006.01)

(52) U.S. Cl.
USPC ................................ 514/211.15; 514/211.01

(58) Field of Classification Search
USPC ........................................ 514/211.01, 211.15
See application file for complete search history.

(56) References Cited

U.S. PATENT DOCUMENTS

| | | | |
|---|---|---|---|
| 8,207,164 B2 * | 6/2012 | Holzer et al. ............... | 514/233.2 |
| 8,338,413 B1 * | 12/2012 | Rueeger ...................... | 514/233.2 |
| 2011/0021520 A1 | 1/2011 | Badiger et al. | |
| 2011/0312937 A1 * | 12/2011 | Banner et al. ............ | 514/211.09 |
| 2012/0238548 A1 * | 9/2012 | Gabellieri et al. ....... | 514/211.15 |

FOREIGN PATENT DOCUMENTS

| WO | 2011/009943 | 1/2011 |
|---|---|---|
| WO | 2011/138293 | 11/2011 |
| WO | 2012/006953 | 1/2012 |

OTHER PUBLICATIONS (International Search Report fo PCT/EP2012/052420 dated May 15, 2012).
Woodard-Grice et al., "J. Biol. Chem." 283(39):26364-26373 ( 2008).
Kuhn et al., "J. Biol. Chem." 282(16):11982-11995 ( 2007).
Akpinar et al., Cell Metab. 2:385-397 ( 2005).
Kiljanski et al., "Thyroid" 15(7):645-652 ( 2005).
Luo et al., "Nature Neuroscience" 3:231-232 ( 2001).
Koistinen et al., "Muscle & Nerve" 34(4):444-450 ( 2006).
Toegel et al., "Osteoarthritis & Cartilage" 18(2):240-248 ( 2010).
Hodges et al., Hum. Mol. Genet. 15:965-977 ( 2006).
Talantov et al., Clin. Cancer Res. 11:7234-7242 ( 2005).
Vassar et al., BACE, Science 286:735 ( 1999).
Greenberg et al., Ann. Neurol. 57:664-678 ( 2005).
Sugimoto et al., "J. Biol. Chem." 282(48):34896-34903 ( 2007).
Roberds et al., Hum. Mol. Genet. 10(12):1317-1324 ( 2001).
Hedlund et al., Cancer Research 68(2):388-394 ( 2008).
Lagos et al., "Blood" 109(4)1 550-1558 ( 2007).
Desnues et al., Clin. Vaccine Immunol. 13:170-178 ( 2006).
Selkoe et al., "Annual Review Cell Biology" 10:373-403 ( 1994).
Basset et al., Scand. J. Immunol. 51:307-311 ( 2000).
Hussain et al., "Molecular & Cellular Neurosciences" 16:609-619 ( 2000).
Prentki et al., J. Clin. Investig. 116(7):1802-1812 ( 2006).
Vattemi et al., "Lancet" 358 (9297):1962-1964 ( 2001).
Maugeri et al., "Srp Arh Celok Lek" ((Suppl. 1)), 138:50-52 ( 2010).
Gatchel et al., Proc. Natl. Acad. Sci. USA 105:1291-1296 ( 2008).
McConlogue et al., "J. Biol. Chem." 282(36):26326-26334 ( 2007).
Wild et al., "Diabetes Care" 27(5):1047-1053 ( 2004).
Kondoh et al., "Breast Cancer & Research Treatment" 78(1):37-44 ( 2003).
Zimmet et al., Nature 414:782-787 ( 2001).
Kihara et al., Proc. Natl. Acad. Sci. USA 106:21807-21812 ( 2009).
Hoffmeister et al., "Journal of the Pancreas" 10(5):501-506 ( 2009).
Finzi et al., "Ultrastruct. Pathol." 32(6):246-251 ( 2008).
Hardy et al., "Science" ((5580)), 297:353-356.
Barbiero et al., Exp. Neurol. 182:335-345 ( 2003).
Baggio et al., Annu. Rev. Med. 57:265-281 ( 2006).
Li et al., "Aging Cell" 5(2):153-165 ( 2006).
Merten et al., "Zeitschrift fur Kardiologie" ((English language Summary is attached to the reference)), 93(11):855-863 ( 2004).
Grewal et al., Mol. Cell Biol. 26:4970-4981 ( 2006).
Lichtenthaler et al., "J. Biol. Chem." 278(49):48713-48719 ( 2003).
Kim et al., "Neurobiology of Disease" 22(2):346-356 ( 2006).

* cited by examiner

*Primary Examiner* — My-Chau T Tran

(57) ABSTRACT

This invention relates to compounds of the formula

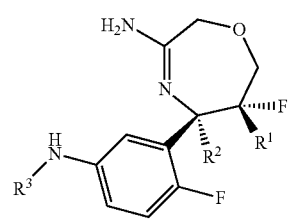

I wherein and $R^1$ to $R^3$ are as described herein, or to pharmaceutically acceptable salts thereof. These compounds are BACE1 and/or BACE2 inhibitors and can be used as pharmaceuticals for the therapeutic and/or prophylactic treatment of diseases such as Alzheimer's disease, diabetes, particularly type 2 diabetes, and other metabolic disorders.

8 Claims, No Drawings

1,4-OXAZEPINES AS BACE1 AND/OR BACE2 INHIBITORS

PRIORITY TO RELATED APPLICATION(S)

This application claims the benefit of European Patent Application No 11155051.3, filed Feb. 18, 2011, which is hereby incorporated by reference in its entirety.

BACKGROUND OF THE INVENTION

Alzheimer's disease (AD) is a neurodegenerative disorder of the central nervous system and the leading cause of a progressive dementia in the elderly population. Its clinical symptoms are impairment of memory, cognition, temporal and local orientation, judgment and reasoning but also severe emotional disturbances. There are currently no treatments available which can prevent the disease or its progression or stably reverse its clinical symptoms. AD has become a major health problem in all societies with high life expectancies and also a significant economic burden for their health systems.

AD is characterized by two major pathologies in the central nervous system (CNS), the occurrence of amyloid plaques and neurofibrillar tangles (Hardy et al., The amyloid hypothesis of Alzheimer's disease: progress and problems on the road to therapeutics, *Science*. 2002 Jul. 19; 297(5580:353-6, Selkoe, Cell biology of the amyloid beta-protein precursor and the mechanism of Alzheimer's disease, *Annu Rev Cell Biol*. 1994; 10:373-403). Both pathologies are also commonly observed in patients with Down's syndrome (trisomy 21), which also develop AD-like symptoms in early life. Neurofibrillar tangles are intracellular aggregates of the microtubule-associated protein tau (MAPT). Amyloid plaques occur in the extracellular space; their principal components are Aβ-peptides. The latter are a group of proteolytic fragments derived from the β-amyloid precursor protein (APP) by a series of proteolytic cleavage steps. Several forms of APP have been identified of which the most abundant are proteins of 695, 751 and 770 amino acids length. They all arise from a single gene through differential splicing. The Aβ-peptides are derived from the same domain of the APP but differ at their N- and C-termini, the main species are of 40 and 42 amino-acid length. There are several lines of evidence which strongly suggest that aggregated Aβ-peptides are the essential molecules in the pathogenesis of AD: 1) amyloid plaques formed of Aβ-peptides are invariably part of the AD pathology; 2) Aβ-peptides are toxic for neurons; 3) in Familial Alzheimer's Disease (FAD) the mutations in the disease genes APP, PSN1, PSN2 lead to increased levels of Aβ-peptides and early brain amyloidosis; 4) transgenic mice which express such FAD genes develop a pathology which bears many resemblances to the human disease. Aβ-peptides are produced from APP through the sequential action of 2 proteolytic enzymes termed β- and γ-secretase. β-Secretase cleaves first in the extracellular domain of APP approximately 28 amino acids outside of the trans-membrane domain (TM) to produce a C-terminal fragment of APP containing the TM- and the cytoplasmatic domain (CTFβ). CTFβ is the substrate for γ-secretase which cleaves at several adjacent positions within the TM to produce the Aβ peptides and the cytoplasmic fragment. The γ-secretase is a complex of at least four different proteins, its catalytic subunit is very likely a presenilin protein (PSEN1, PSEN2). The β-secretase (BACE1, Asp2; BACE stands for β-site APP-cleaving enzyme) is an aspartyl protease which is anchored into the membrane by a transmembrane domain (Vassar et al., Beta-secretase cleavage of Alzheimer's amyloid precursor protein by the transmembrane aspartic protease BACE, *Science*. 1999 Oct. 22; 286(5440): 735). It is expressed in many tissues of the human organism but its level is especially high in the CNS. Genetic ablation of the BACE1 gene in mice has clearly shown that its activity is essential for the processing of APP which leads to the generation of Aβ-peptides, in the absence of BACE1 no Aβ-peptides are produced (Luo et al., Mice deficient in BACE1, the Alzheimer's beta-secretase, have normal phenotype and abolished beta-amyloid generation, *Nat Neurosci*. 2001 March; 4(3):231-2, Roberds et al., BACE knockout mice are healthy despite lacking the primary beta-secretase activity in brain: implications for Alzheimer's disease therapeutics, *Hum Mol. Genet*. 2001 Jun. 1; 10(12): 1317-24). Mice which have been genetically engineered to express the human APP gene and which form extensive amyloid plaques and Alzheimer's disease like pathologies during aging fail to do so when β-secretase activity is reduced by genetic ablation of one of the BACE1 alleles (McConlogue et al., Partial reduction of BACE1 has dramatic effects on Alzheimer plaque and synaptic pathology in APP Transgenic Mice. *J Biol. Chem*. 2007 Sep. 7; 282(36):26326). It is thus presumed that inhibitors of BACE1 activity can be useful agents for therapeutic intervention in AD.

Type 2 diabetes (T2D) is caused by insulin resistance and inadequate insulin secretion from pancreatic β-cells leading to poor blood-glucose control and hyperglycemia (M Prentki & CJ Nolan, "Islet beta-cell failure in type 2 diabetes." J. Clin. Investig. 2006, 116(7), 1802-1812). Patients with T2D have an increased risk of microvascular and macrovascular disease and a range of related complications including diabetic nephropathy, retinopathy and cardiovascular disease. In 2000, an estimated 171 million people had the condition with the expectation that this figure will double by 2030 (S Wild, G Roglic, A Green, R. Sicree & H King, "Global prevalence of diabetes", Diabetes Care 2004, 27(5), 1047-1053), making the disease a major healthcare problem. The rise in prevalence of T2D is associated with an increasingly sedentary lifestyle and high-energy food intake of the world's population (P Zimmet, KGMM Alberti & J Shaw, "Global and societal implications of the diabetes epidemic" Nature 2001, 414, 782-787).

β-Cell failure and consequent dramatic decline in insulin secretion and hyperglycemia marks the onset of T2D. Most current treatments do not prevent the loss of β-cell mass characterizing overt T2D. However, recent developments with GLP-1 analogues, gastrin and other agents show that preservation and proliferation of β-cells is possible to achieve, leading to an improved glucose tolerance and slower progression to overt T2D (LL Baggio & DJ Drucker, "Therapeutic approaches to preserve islet mass in type 2 diabetes", Annu. Rev. Med. 2006, 57, 265-281).

Tmem27 has been identified as a protein promoting beta-cell proliferation (P Akpinar, S Kuwajima, J Krützfeldt, M Stoffel, "Tmem27: A cleaved and shed plasma membrane protein that stimulates pancreatic β cell proliferation", Cell Metab. 2005, 2, 385-397) and insulin secretion (K Fukui, Q Yang, Y Cao, N Takahashi et al., "The HNF-1 target Collectrin controls insulin exocytosis by SNARE complex formation", Cell Metab. 2005, 2, 373-384). Tmem27 is a 42 kDa membrane glycoprotein which is constitutively shed from the surface of β-cells, resulting from a degradation of the full-length cellular Tmem27. Overexpression of Tmem27 in a transgenic mouse increases β-cell mass and improves glucose tolerance in a diet-induced obesity DIO model of diabetes. Furthermore, siRNA knockout of Tmem27 in a rodent β-cell proliferation assay (e.g. using INS1e cells) reduces the proliferation rate, indicating a role for Tmem27 in control of β-cell mass.

In the same proliferation assay, BACE2 inhibitors also increase proliferation. However, BACE2 inhibition combined with Tmem27 siRNA knockdown results in low proliferation rates. Therefore, it is concluded that BACE2 is the protease responsible for the degradation of Tmem27. Furthermore, in vitro, BACE2 cleaves a peptide based on the sequence of Tmem27. The closely related protease BACE1 does not cleave this peptide and selective inhibition of BACE1 alone does not enhance proliferation of β-cells.

The close homolog BACE2 is a membrane-bound aspartyl protease and is co-localized with Tmem27 in human pancreatic β-cells (G Finzi, F Franzi, C Placidi, F Acquati et al., "BACE2 is stored in secretory granules of mouse and rat pancreatic beta cells", Ultrastruct Pathol. 2008, 32(6), 246-251). It is also known to be capable of degrading APP (I Hussain, D Powell, D Howlett, G Chapman et al., "ASP1 (BACE2) cleaves the amyloid precursor protein at the β-secretase site" Mol Cell Neurosci. 2000, 16, 609-619), IL-1R2 (P Kuhn, E Marjaux, A Imhof, B De Strooper et al., "Regulated intramembrane proteolysis of the interleukin-1 receptor II by alpha-, beta-, and gamma-secretase" J. Biol. Chem. 2007, 282(16), 11982-11995) and ACE2. The capability to degrade ACE2 indicates a possible role of BACE2 in the control of hypertension.

Inhibitors of BACE1 and/or BACE2 can in addition be used to treat the following diseases: IBM (inclusion body myositis) (Vattemi G. et al., Lancet. 2001 Dec. 8; 358(9297): 1962-4), Down's Syndrome (Barbiero L. et al, Exp Neurol. 2003 August; 182(2):335-45), Wilson's Disease (Sugimoto I. et al., J Biol. Chem. 2007 Nov. 30; 282(48):34896-903), Whipple's disease (Desnues B. et al., Clin Vaccine Immunol. 2006 February; 13(2):170-8), SpinoCerebellar Ataxia 1 and SpinoCerebellar Ataxia 7 (Gatchel J. R. et al., Proc Natl Acad Sci U S A 2008 Jan. 29; 105(4):1291-6), Dermatomyositis (Greenberg S. A. et al., Ann Neurol. 2005 Can; 57(5):664-78 and Greenberg S. A. et al., Neurol 2005 Can; 57(5):664-78), Kaposi Sarcoma (Lagos D. et al, Blood, 2007 Feb. 15; 109 (4):1550-8), Glioblastoma multiforme (E-MEXP-2576, http://www.ebi.ac.uk/microarray-as/aer/resurt?queryFor=PhysicalArrayDesign &aAccession=A-MEXP-258), Rheumatoid arthritis (Ungethuem U. et al, GSE2053), Amyotrophic lateral sclerosis (Koistinen H. et al., Muscle Nerve. 2006 October; 34(4):444-50 and Li Q. X. et al, Aging Cell. 2006 April; 5(2):153-65), Huntington's Disease (Kim Y. J. et al., Neurobiol Dis. 2006 Can; 22(2):346-56. Epub 2006 Jan. 19 and Hodges A. et al., Hum Mol Genet. 2006 Mar. 15; 15(6):965-77. Epub 2006 Feb. 8), Multiple Mieloma (Kihara Y. et al, Proc Natl Acad Sci USA. 2009 Dec. 22; 106(51):21807-12), Malignant melanoma (Talantov D. et al, Clin Cancer Res. 2005 Oct. 15; 11(20):7234-42), Sjogren syndrome (Basset C. et al., Scand J. Immunol. 2000 March; 51(3):307-11), Lupus erythematosus (Grewal P. K. et al, Mol Cell Biol. 2006, July; 26(13):4970-81), Macrophagic myofasciitis, juvenile idiopathic arthritis, granulomatous arthritis, Breast cancer (Hedlund M. et al, Cancer Res. 2008 Jan. 15; 68(2):388-94 and Kondoh K. et al., Breast Cancer Res Treat. 2003 March; 78(1):37-44), Gastrointestinal diseases (Hoffmeister A. et al, JOP. 2009 Sep. 4; 10(5):501-6), Autoimmune/inflammatory diseases (Woodard-Grice A. V. et al., J Biol. Chem. 2008 Sep. 26; 283(39):26364-73. Epub 2008 Jul. 23), Rheumatoid Arthritis (Toegel S. et al, Osteoarthritis Cartilage. 2010 February; 18(2):240-8. Epub 2009 Sep. 22), Inflammatory reactions (Lichtenthaler S. F. et al., J Biol. Chem. 2003 Dec. 5; 278(49):48713-9. Epub 2003 Sep. 24), Arterial Thrombosis (Merten M. et al., Z Kardiol. 2004 November; 93(11):855-63), Cardiovascular diseases such as Myocardial infarction and stroke (Maugeri N. et al., Srp Arh Celok Lek. 2010 January; 138 Suppl 1:50-2) and Graves disease (Kiljański J. et al, Thyroid. 2005 July; 15(7):645-52).

SUMMARY OF THE INVENTION

The present invention provides 2,5,6,7-tetrahydro-[1,4]oxazepin-3-ylamines having BACE1 and/or BACE2 inhibitory properties, their manufacture, pharmaceutical compositions containing them and their use as therapeutically active substances.

In particular, the present invention provides compounds of the formula

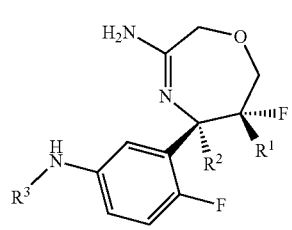

wherein $R^1$ to $R^3$ are as described below, or to pharmaceutically acceptable salts thereof.

The compounds of the invention have Asp2 (β-secretase, BACE1 or Memapsin-2) inhibitory activity and can therefore be used in the therapeutic and/or prophylactic treatment of diseases and disorders characterized by elevated (3-amyloid levels and/or (3-amyloid oligomers and/or β-amyloid plaques and further deposits, particularly Alzheimer's disease. In addition, the compounds of formula I have BACE2 inhibitory activity and can therefore be used in the therapeutic and/or prophylactic treatment of diseases and disorders such as type 2 diabetes and other metabolic disorders.

The present invention to provides selective BACE1 inhibitors with enhanced therapeutic and pharmacological properties compared to the compounds already known in the art. The formation, or formation and deposition, of β-amyloid plaques in, on or around neurological tissue (e.g., the brain) is inhibited by such compounds by blocking the Aβ production from APP or an APP fragment. Therefore, such compounds are useful as therapeutically active substances, particularly in the control or prevention of Alzheimer's disease.

Inhibition of BACE2 is proposed as a treatment for type 2 diabetes (T2D) with the potential to preserve and restore β-cell mass and stimulate insulin secretion in pre-diabetic and diabetic patients. Therefore, the present invention provides selective BACE2 inhibitors with enhanced therapeutic and pharmacological properties compared to the compounds already known in the art. Such compounds are useful as therapeutically active substances, particularly in the treatment and/or prevention of diseases which are associated with the inhibition of BACE2 such as type 2 diabetes.

DETAILED DESCRIPTION OF THE INVENTION

The present invention provides novel compounds of formula I having BACE1 and/or BACE2 inhibitory properties, their manufacture, pharmaceutical compositions containing the compounds of the present invention, the production of such pharmaceutical compositions as well as the use of the compounds of formula I in the treatment or prevention of diseases such as Alzheimer's disease and type 2 diabetes.

Unless otherwise indicated, the following definitions are set forth to illustrate and define the meaning and scope of the various terms used to describe the invention.

The term "halogen", alone or in combination with other groups, refers to fluoro, chloro, bromo and iodo, in particular fluoro (F).

The term "amidyl", alone or in combination with other groups, refers to —C(=O)—NH$_2$.

The term "$C_{1-7}$-alkyl", alone or in combination with other groups, signifies a straight-chain or branched-chain hydrocarbon group with 1 to 7 carbon atoms, in particular a straight or branched-chain hydrocarbon group with 1 to 6 carbon atoms and more particularly a straight or branched-chain hydrocarbon group with 1 to 4 carbon atoms. Examples of straight-chain and branched $C_{1-7}$ alkyl groups are methyl, ethyl, propyl, isopropyl, butyl, isobutyl, tert.-butyl, the isomeric pentyls, the isomeric hexyls and the isomeric heptyls, in particular methyl (Me) and ethyl (Et). More particular is methyl.

The term "$C_{1-7}$-alkoxy", alone or in combination with other groups, refers to the group R'—O—, wherein R' is $C_{1-7}$-alkyl as described herein. Examples of "$C_{1-7}$-alkoxy" include methoxy, ethoxy, n-propoxy, isopropoxy, n-butoxy, isobutoxy, sec.-butoxy and tert.-butoxy, preferably methoxy (MeO).

The term "$C_{3-7}$-cycloalkyl", alone or in combination with other groups, denotes a monovalent saturated monocyclic or bicyclic hydrocarbon group of 3 to 7 ring carbon atoms, particularly a monovalent saturated monocyclic hydrocarbon group of 3 to 5 ring carbon atoms. Bicyclic means consisting of two saturated carbocycles having two carbon atoms in common, i.e. the bridge separating the two rings is either a single bond or a chain of one or two carbon atoms. Particular $C_{3-7}$-cycloalkyl groups are monocyclic. Examples are cyclopropyl, cyclobutanyl, cyclopentyl, cyclohexyl or cycloheptyl. Examples for bicyclic cycloalkyl are bicyclo[2.2.1]heptanyl, bicyclo[2.2.2]octanyl or adamantanyl. Particular "$C_{3-7}$-cycloalkyl" is cyclopropyl.

The term "heteroaryl", alone or in combination with other groups, refers to a cyclic aromatic group having a single 4 to 8 membered ring or multiple condensed rings containing 6 to 14, in particular 6 to 10, ring atoms and containing 1, 2 or 3 heteroatoms individually selected from N, O and S, in particular N and O, in which group at least one heterocyclic ring is aromatic. Examples of "heteroaryl" include benzofuryl, benzoimidazolyl, 1H-benzoimidazolyl, benzooxazinyl, benzoxazolyl, benzothiazinyl, benzothiazolyl, benzothienyl, benzotriazolyl, furyl, imidazolyl, indazolyl, 1H-indazolyl, indolyl, isoquinolinyl, isothiazolyl, isoxazolyl, oxazolyl, pyrazinyl, pyrazolyl (pyrazyl), 1H-pyrazolyl, pyrazolo[1,5-a]pyridinyl, pyridazinyl, pyridinyl, pyrimidinyl, pyrrolyl, quinolinyl, tetrazolyl, thiazolyl, thienyl, triazolyl, 6,7-dihydro-5H-[1]pyrindinyl and the like. Particular "heteroaryl" are pyridinyl, oxazolyl, pyrazinyl and thiazolyl. Specific examples are pyridine-2-yl, oxazol-4-yl, pyrazin-2-yl and thiazol-2-yl.

The term "$C_{2-7}$-alkynyl", alone or in combination with other groups, denotes a monovalent linear or branched hydrocarbon group of 2 to 7 carbon atoms, in particular from 2 to 4 carbon atoms, containing one, two or three triple bonds. Examples of $C_{2-7}$-alkynyl include ethynyl, propynyl, prop-2-ynyl, isopropynyl and n-butynyl. Specific examples are ethynyl and propynyl.

The term "$C_{1-7}$-alkoxy-$C_{2-7}$-alkynyl", alone or in combination with other groups, refers to a "$C_{1-7}$-alkoxy" as defined herein linked via a "$C_{2-7}$-alkynyl" as defined herein. A specific example is 3-methoxy-prop-1-ynyl.

The term "$C_{3-7}$-cycloalkyl-$C_{2-7}$-alkynyl", alone or in combination with other groups, refers to a "$C_{3-7}$-cycloalkyl" as defined herein linked via a "$C_{2-7}$-alkynyl" as defined herein. A specific example is cyclopropylethynyl.

The term "$C_{3-7}$-cycloalkyl-$C_{1-7}$-alkoxy", alone or in combination with other groups, refers to a "$C_{3-7}$-cycloalkyl" as defined herein linked via a "$C_{1-7}$-alkoxy" as defined herein. A specific example is cyclopropylmethoxy.

The term "$C_{3-7}$-cycloalkyl-$C_{1-7}$-alkyl", alone or in combination with other groups, refers to a "$C_{3-7}$-cycloalkyl" as defined herein linked via a "$C_{1-7}$-alkyl" as defined herein. A specific example is cyclopropylmethyl.

The term "$C_{1-7}$-alkyl-S-", alone or in combination with other groups, refers to a $C_{1-7}$-alkyl as defined herein linked via —S—.

The term "coupling agent" refers to an agent selected from the group consisting of carbodiimides or uronium salts, such as for example N,N'-carbonyldiimidazole (CDI), N,N'-dicyclohexylcarbodiimide (DCC), N-(3-dimethylaminopropyl)-N'-ethyl-carbodiimide-hydrochloride (EDCI), O-(benzotriazol-1-yl)-N,N,N,N-tetramethyluronium tetrafluoroborate (TBTU) and 1-[bis(dimethylamino)methylene]-1H-1,2,3-triazolo[4,5-b]pyridinium-3-oxide hexafluorophosphate (HATU).

The term "under basic conditions", refers to the presence of a base, in particular an alkylamine such as diisopropylethylamine (DIEA) or triethylamine (TEA), or a tertiary amine such as N-methylmorpholine or 4-(dimethylamino)-pyridine.

The term "triazine derivative" for example refers to 4-(4, 6-dimethoxy-1,3,5-triazin-2-yl)-4-methyl-morpholinium-chloride.

The term "protic solvent" refers to a solvent that has a hydrogen atom bound to an oxygen atom as in a hydroxyl group or bound to a nitrogen atom as in an amine group, which hydrogen is dissociable. Examples are alcohols, in particular ethanol or methanol.

The term "polar solvent" refers to molecules whose electric charges are unequally distributed within the molecule. Examples include water and alcohols, in particular methanol.

The term "mild oxidant" refers, for example, to tert-butyl-hydroperoxide.

The term "oxonium salt" refers to salts containing oxonium ($[H_3O^+]$) as cation.

The term "ammonium salt" refers to salts containing ammonium ($[NH_4^+]$) as cation.

The term "pharmaceutically acceptable salts" refers to salts that are suitable for use in contact with the tissues of humans and animals. Examples of suitable salts with inorganic and organic acids are, but are not limited to, acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid, sulphuric acid, tartaric acid, trifluoroacetic acid and the like. The terms "pharmaceutically acceptable carrier" and "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Preferably it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The term "inhibitor" denotes a compound which competes with, reduces or prevents the binding of a particular ligand to particular receptor or which reduces or prevents the inhibition of the function of a particular protein.

The term "half maximal inhibitory concentration" ($IC_{50}$) denotes the concentration of a particular compound required for obtaining 50% inhibition of a biological process in vitro. $IC_{50}$ values can be converted logarithmically to $pIC_{50}$ values ($-\log IC_{50}$), in which higher values indicate exponentially greater potency. The $IC_{50}$ value is not an absolute value but depends on experimental conditions e.g. concentrations employed. The $IC_{50}$ value can be converted to an absolute inhibition constant (Ki) using the Cheng-Prusoff equation (Biochem. Pharmacol. (1973) 22:3099). The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values ($-\log$ Ki), in which higher values indicate exponentially greater potency.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as preferred, more preferred and most preferred definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product can not necessarily result directly from the combination of two reagents which were initially added, i.e., there can be one or more intermediates which are produced in the mixture which ultimately leads to the formation of the indicated and/or the desired product. The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

The compounds of formula I can also be solvated, e.g., hydrated. The solvation can be effected in the course of the manufacturing process or can take place e.g. as a consequence of hygroscopic properties of an initially anhydrous compound of formula I (hydration). The term "pharmaceutically acceptable salts" also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four non-identical substituents is termed a "chiral center". Whenever a chiral carbon is present in a chemical structure, it is intended that all stereoisomers associated with that chiral carbon are encompassed by the structure.

All separate embodiments can be combined.

The present invention provides compounds of the formula

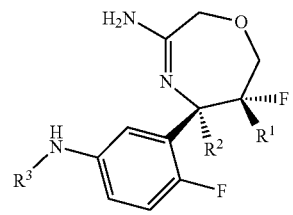

I wherein
$R^1$ is H or F;
$R^2$ is $C_{1-7}$-alkyl; and
$R^3$ is —(C=O)—$R^4$ or $R^5$, wherein
  $R^4$ is heteroaryl substituted by one substituent selected from the group consisting of $C_{3-7}$-cycloalkyl-$C_{1-7}$-alkoxy-, $C_{3-7}$-cycloalkyl-$C_{2-7}$-alkynyl-, $C_{1-7}$-alkoxy-$C_{2-7}$-alkynyl-, unsubstituted heteroaryl, unsubstituted $C_{3-7}$-cycloalkyl and $C_{1-7}$-alkyl-S—, or
  $R^4$ is heteroaryl substituted by one halogen and one amidyl; and
  $R^5$ is $C_{3-7}$-cycloalkyl-$C_{1-7}$-alkyl-;
or a pharmaceutically acceptable salt thereof.

A certain embodiment provides a compound of formula I as described herein, wherein
$R^1$ is F;
$R^2$ is Me; and
$R^3$ is —(C=O)—$R^4$, wherein
  $R^4$ is pyridinyl substituted by one substituent selected from the group consisting of $C_{3-7}$-cycloalkyl-$C_{1-7}$-alkoxy-, $C_{3-7}$-cycloalkyl-$C_{2-7}$-alkynyl-, $C_{1-7}$-alkoxy-$C_{2-7}$-alkynyl-, or
  $R^4$ is pyridinyl substituted by one F and one amidyl;
or a pharmaceutically acceptable salt thereof.

A certain embodiment provides a compound of formula I as described herein, wherein $R^1$ is F, $R^2$ is Me, $R^3$ is —(C=O)—$R^4$ and $R^4$ is 3-fluoro-5-amido-pyridin-2-yl, 6-(cyclopropylmethoxy)-pyridin-2-yl, 5-(cyclopropylethynyl)-pyridin-2-yl or 5-(3-methoxyprop-1-ynyl)-pyridin-2-yl.

A certain embodiment provides a compound of formula I as described herein, wherein $R^1$ is F.

A certain embodiment provides a compound of formula I as described herein, wherein $R^1$ is H.

A certain embodiment provides a compound of formula I as described herein, wherein $R^2$ is Me.

A certain embodiment provides a compound of formula I as described herein, wherein $R^2$ is Et.

A certain embodiment provides a compound of formula I as described herein, wherein $R^3$ is $C_{3-7}$-cycloalkyl-$C_{1-7}$-alkyl-.

A certain embodiment provides a compound of formula I as described herein, wherein $R^3$ is cyclopropyl-$CH_2$—.

A certain embodiment provides a compound of formula I as described herein, which is (5R,6R)-5-[5-(Cyclopropylmethyl-amino)-2-fluoro-phenyl]-6-fluoro-5-methyl-2,5,6,7-tetrahydro-[1,4]oxazepin-3-ylamine.

A certain embodiment provides a compound of formula I as described herein, wherein $R^3$ is —(C=O)—$R^4$.

A certain embodiment provides a compound of formula I as described herein, wherein $R^4$ is pyridinyl substituted by one halogen and one amidyl.

A certain embodiment provides a compound of formula I as described herein, wherein $R^4$ is pyridinyl substituted by one F and one amidyl.

A certain embodiment providesa compound of formula I as described herein, which is (R)—N2-(3-(3-amino-6,6-difluoro-5-methyl-2,5,6,7-tetrahydro-1,4-oxazepin-5-yl)-4-fluorophenyl)-3-fluoropyridine-2,5-dicarboxamide formate.

A certain embodiment providesa compound of formula I as described herein, wherein $R^4$ is pyridinyl substituted by one substituent selected from the group consisting of $C_{3-7}$-cycloalkyl-$C_{1-7}$-alkoxy-, $C_{3-7}$-cycloalkyl-$C_{2-7}$-alkynyl-, $C_{1-7}$-alkoxy-$C_{2-7}$-alkynyl-, unsubstituted heteroaryl and unsubstituted $C_{3-7}$-cycloalkyl.

A certain embodiment providesa compound of formula I as described herein, wherein $R^4$ is pyridinyl substituted by $C_{3-7}$-cycloalkyl-$C_{1-7}$-alkoxy-.

A certain embodiment provides a compound of formula I as described herein, wherein $R^4$ is pyridinyl substituted by $C_{3-7}$-cycloalkyl-$C_{2-7}$-alkynyl-.

A certain embodiment provides a compound of formula I as described herein, wherein $R^4$ is pyridinyl substituted by $C_{1-7}$-alkoxy-$C_{2-7}$-alkynyl-.

A certain embodiment provides a compound of formula I as described herein, wherein $R^4$ is pyridinyl substituted by unsubstituted heteroaryl.

A certain embodiment provides a compound of formula I as described herein, wherein $R^4$ is pyridinyl substituted by unsubstituted thiazol-2-yl.

A certain embodiment provides a compound of formula I as described herein, wherein $R^4$ is pyridinyl substituted by unsubstituted $C_{3-7}$-cycloalkyl.

A certain embodiment provides a compound of formula I as described herein, wherein $R^4$ is pyridinyl substituted by unsubstituted cyclopropyl.

A certain embodiment provides a compound of formula I as described herein, selected from the group consisting of
(R)—N-(3-(3-amino-6,6-difluoro-5-methyl-2,5,6,7-tetrahydro-1,4-oxazepin-5-yl)-4-fluorophenyl)-6-(cyclopropylmethoxy)picolinamide formate,
(R)—N-(3-(3-amino-6,6-difluoro-5-methyl-2,5,6,7-tetrahydro-1,4-oxazepin-5-yl)-4-fluorophenyl)-5-(thiazol-2-yl)picolinamide formate,
(R)—N-(3-(3-amino-6,6-difluoro-5-methyl-2,5,6,7-tetrahydro-1,4-oxazepin-5-yl)-4-fluorophenyl)-5-(cyclopropylethynyl)picolinamide formate,
(R)—N-(3-(3-amino-6,6-difluoro-5-methyl-2,5,6,7-tetrahydro-1,4-oxazepin-5-yl)-4-fluorophenyl)-5-cyclopropylpicolinamide formate, and
(R)—N-(3-(3-amino-6,6-difluoro-5-methyl-2,5,6,7-tetrahydro-1,4-oxazepin-5-yl)-4-fluorophenyl)-5-(3-methoxyprop-1-ynyl)picolinamide formate.

A certain embodiment provides a compound of formula I as described herein, which is (R)—N-(3-(3-amino-6,6-difluoro-5-methyl-2,5,6,7-tetrahydro-1,4-oxazepin-5-yl)-4-fluorophenyl)-6-(cyclopropylmethoxy)picolinamide formate.

A certain embodiment provides a compound of formula I as described herein, which is (R)—N-(3-(3-amino-6,6-difluoro-5-methyl-2,5,6,7-tetrahydro-1,4-oxazepin-5-yl)-4-fluorophenyl)-5-(thiazol-2-yl)picolinamide formate.

A certain embodiment provides a compound of formula I as described herein, which is (R)—N-(3-(3-amino-6,6-difluoro-5-methyl-2,5,6,7-tetrahydro-1,4-oxazepin-5-yl)-4-fluorophenyl)-5-(cyclopropylethynyl)picolinamide formate.

A certain embodiment provides a compound of formula I as described herein, which is (R)—N-(3-(3-amino-6,6-difluoro-5-methyl-2,5,6,7-tetrahydro-1,4-oxazepin-5-yl)-4-fluorophenyl)-5-cyclopropylpicolinamide formate.

A certain embodiment provides a compound of formula I as described herein, which is (R)—N-(3-(3-amino-6,6-difluoro-5-methyl-2,5,6,7-tetrahydro-1,4-oxazepin-5-yl)-4-fluorophenyl)-5-(3-methoxyprop-1-ynyl)picolinamide formate.

A certain embodiment provides a compound of formula I as described herein, wherein $R^4$ is pyrazinyl substituted by $C_{1-7}$-alkyl-S—.

A certain embodiment provides a compound of formula I as described herein, wherein $R^4$ is pyrazinyl substituted by methyl-S—.

A certain embodiment provides a compound of formula I as described herein, which is (R)—N-(3-(3-amino-6,6-difluoro-5-methyl-2,5,6,7-tetrahydro-1,4-oxazepin-5-yl)-4-fluorophenyl)-5-(methylthio)pyrazine-2-carboxamide formate.

A certain embodiment provides a compound of formula I as described herein, wherein $R^4$ is oxazolyl substituted by $C_{3-7}$-cycloalkyl.

A certain embodiment provides a compound of formula I as described herein, wherein $R^4$ is oxazolyl substituted by cyclopropyl.

A certain embodiment provides a compound of formula I as described herein, which is (R)—N-(3-(3-amino-5-ethyl-6,6-difluoro-2,5,6,7-tetrahydro-1,4-oxazepin-5-yl)-4-fluorophenyl)-5-cyclopropyloxazole-4-carboxamide.

A certain embodiment provides a compound of formula I as described herein, selected from the group consisting of
(R)—N2-(3-(3-amino-6,6-difluoro-5-methyl-2,5,6,7-tetrahydro-1,4-oxazepin-5-yl)-4-fluorophenyl)-3-fluoropyridine-2,5-dicarboxamide formate,
(R)—N-(3-(3-amino-6,6-difluoro-5-methyl-2,5,6,7-tetrahydro-1,4-oxazepin-5-yl)-4-fluorophenyl)-6-(cyclopropylmethoxy)picolinamide formate,
(R)—N-(3-(3-amino-6,6-difluoro-5-methyl-2,5,6,7-tetrahydro-1,4-oxazepin-5-yl)-4-fluorophenyl)-5-(cyclopropylethynyl)picolinamide formate,
(R)—N-(3-(3-amino-6,6-difluoro-5-methyl-2,5,6,7-tetrahydro-1,4-oxazepin-5-yl)-4-fluorophenyl)-5-(3-methoxyprop-1-ynyl)picolinamide formate, and
(5R,6R)-5-[5-(Cyclopropylmethyl-amino)-2-fluoro-phenyl]-6-fluoro-5-methyl-2,5,6,7-tetrahydro-[1,4]oxazepin-3-ylamine.

A certain embodiment provides a compound of formula I as described herein, selected from the group consisting of
(R)—N2-(3-(3-amino-6,6-difluoro-5-methyl-2,5,6,7-tetrahydro-1,4-oxazepin-5-yl)-4-fluorophenyl)-3-fluoropyridine-2,5-dicarboxamide formate,
(R)—N-(3-(3-amino-6,6-difluoro-5-methyl-2,5,6,7-tetrahydro-1,4-oxazepin-5-yl)-4-fluorophenyl)-6-(cyclopropylmethoxy)picolinamide formate,
(R)—N-(3-(3-amino-6,6-difluoro-5-methyl-2,5,6,7-tetrahydro-1,4-oxazepin-5-yl)-4-fluorophenyl)-5-(cyclopropylethynyl)picolinamide formate, and (R)—N-(3-(3-amino-6,6-difluoro-5-methyl-2,5,6,7-tetrahydro-1,4-oxazepin-5-yl)-4-fluorophenyl)-5-(3-methoxyprop-1-ynyl)picolinamide formate.

A certain embodiment provides a process for the manufacture of compounds of formula I as defined herein, which process comprises
a) reacting an amine of the formula II with a carboxylic acid of the formula III in the presence of a coupling reagent under basic conditions or with the help of a triazine derivative to obtain a compound of formula Ia

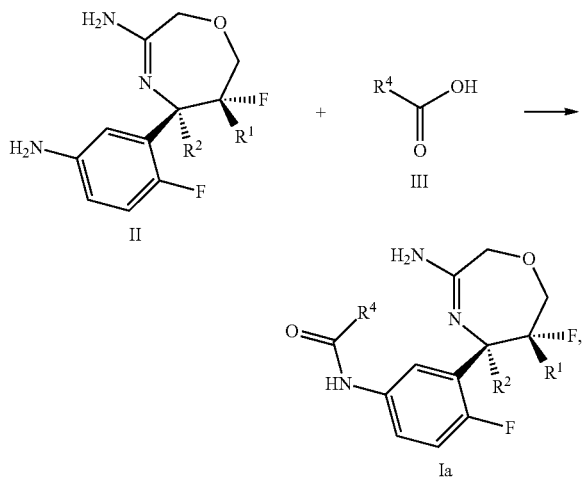

wherein $R^1$, $R^2$ and $R^4$ are as defined herein, or alternatively,
b) reacting an amine of the formula II with a compound of formula IV, wherein R is hydrogen or $C_{1-7}$-alkyl, in the presence of acetic acid and sodium triacetoxyborohydride to obtain a compound of formula Ib

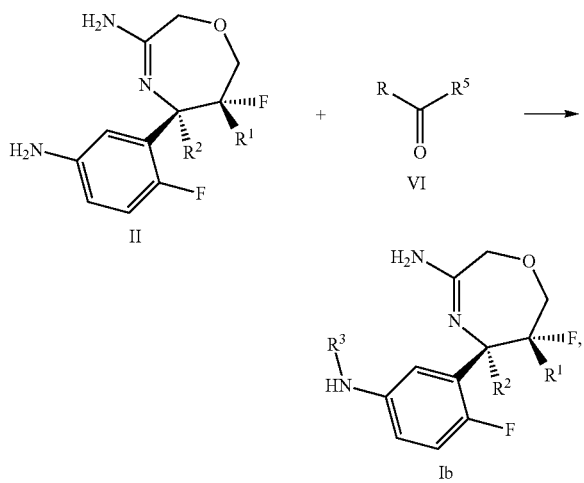

wherein $R^1$, $R^2$, $R^3$ and $R^5$ are as defined herein.

The invention further provides a compound of formula I as defined above obtainable according to a process as defined herein.

A certain embodiment of the invention provides a compound of formula I as defined herein and a pharmaceutically acceptable carrier and/or excipient.

A certain embodiment of the invention provides a compound of formula I as defined herein for use as medicaments.

A certain embodiment of the invention provides a compound of formula I as defined herein for use in the therapeutic and/or prophylactic treatment of Alzheimer's disease and/or type 2 diabetes.

A certain embodiment of the invention provides a compound of formula I as defined herein for use in the therapeutic and/or prophylactic treatment of Alzheimer's disease.

A certain embodiment of the invention provides a compound of formula I as defined herein for use in the therapeutic and/or prophylactic treatment of type 2 diabetes.

A certain embodiment of the invention provides a compound of formula I as defined herein for the use as therapeutically active substance for the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease.

A certain embodiment of the invention provides a compound of formula I as defined herein for the preparation of medicaments for the therapeutic and/or prophylactic treatment of Alzheimer's disease and/or type 2 diabetes.

A certain embodiment of the invention provides a compound of formula I as defined herein for the preparation of medicaments for the therapeutic and/or prophylactic treatment of Alzheimer's disease.

A certain embodiment of the invention provides a compound of formula I as defined herein for the preparation of medicaments for the therapeutic and/or prophylactic treatment of type 2 diabetes.

A certain embodiment of the invention provides a method for the therapeutic and/or prophylactic treatment of diseases which can be ameliorated with the inhibition of BACE1 and/or BACE 2 activity, particularly for the treatment of Alzheimer's disease and type 2 diabetes, which method comprises administering a therapeutically active amount of a compound of formula I as described herein to a human being or animal.

A certain embodiment of the invention provides a compound of formula I as defined herein for use in the manufacture of a medicament for use in the therapeutic and/or prophylactic treatment of Alzheimer's disease and/or type 2 diabetes.

A certain embodiment of the invention provides a compound of formula I as defined herein for the use as therapeutically active substance for the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease.

A certain embodiment of the invention provides a compound of formula I as defined herein for the preparation of medicaments for the therapeutic and/or prophylactic treatment of Alzheimer's disease and/or type 2 diabetes.

A certain embodiment of the invention provides a method for the therapeutic and/or prophylactic treatment of diseases which can be ameliorated with the inhibition of BACE1 and/or BACE 2 activity, particularly for the treatment of Alzheimer's disease and type 2 diabetes, which method comprises administering a therapeutically active amount of a compound of formula I to a human being or animal.

A certain embodiment of the invention provides a method for the therapeutic and/or prophylactic treatment of diseases which can be ameliorated with the inhibition of BACE1 and/or BACE 2 activity, particularly for the treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease which method comprises administering a therapeutically active amount of a compound of formula I to a human being or animal.

As described herein before, the compounds of formula I of the invention will be useful in preserving and restoring beta-cell function and stimulating insulin secretion in diabetic patients and in non-diabetic patients who have impaired glucose tolerance or who are in a pre-diabetic condition. They can be useful in treating type 1 diabetes or in delaying or preventing a patient with type 2 diabetes from needing insulin therapy. The compounds of formula I are further useful to ameliorate hyperinsulinemia, which often occurs in diabetic or pre-diabetic patients and in reducing the risks associated with metabolic syndrome, they can also be useful in treating vascular diseases such as hypertension.

Thus, the expression 'diseases which can be ameliorated with the inhibition of BACE2 activity' means diseases such as metabolic and cardiovascular diseases, in particular diabetes, more particularly type 2 diabetes, gestational diabetes, impaired fasting glucose, impaired glucose tolerance, insulin resistance, pre-diabetes, metabolic syndrome, diabetes type 1, complications of diabetes including diabetic nephropathy, diabetic retinopathy and diabetic neuropathy, chronic kidney disease, dyslipidemia, atherosclerosis, myocardial infarction, hypertension and further metabolic and cardiovascular disorders.

In particular, the expression 'diseases which can be ameliorated with the inhibition of BACE2 activity' relates to diabetes, particularly type 2 diabetes, impaired glucose tolerance, pre-diabetes, metabolic syndrome and hypertension. More particularly, the expression 'diseases which are associated with the inhibition of BACE2 activity' relates to diabetes, particularly type 2 diabetes.

The compounds of formula I can contain one or more asymmetric centers and can therefore occur as racemates, racemic mixtures, single enantiomers, diastereomeric mixtures and individual diastereomers. Additional asymmetric centers can be present depending upon the nature of the various substituents on the molecule. Each such asymmetric centre will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations can be achieved as known in the art by appropriate modification of the methodology disclosed herein. Their absolute stereochemistry can be determined by the x-ray crystallography of crystalline products or crystalline intermediates which are derivatized, if necessary, with a reagent containing an asymmetric centre of known absolute configuration. If desired, racemic mixtures of the compounds can be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

In more detail, compounds of formula I according to the present invention can be prepared by the methods and procedures given below. Some typical procedures for the preparation of compounds of formula I are illustrated in Schemes A ($R^{12}$=H, Br or $NO_2$):

Sulfinyl imines of general formula A2 can be prepared in analogy to T. P. Tang & J. A. Ellman, J. Org. Chem. 1999, 64, 12, by condensation of an aryl ketone and a sulfinamide, e.g. an alkyl sulfinamide, most preferably (R)-(+)-tert-butylsulfinamide in the presence of a Lewis acid such as e.g. a titanium (IV)alkoxyde, more preferably titanium(IV)ethoxide in a solvent such as an ether, e.g. diethyl ether or more preferably THF.

The conversion of the sulfinyl imine A2 to the sulfinamide ester A3 proceeds stereoselectively by the chiral directing group as described by Tang & Ellman. The sulfinyl imine A2 can be reacted with a titanium enolate generated from e.g. an alkyl acetate, preferably ethyl acetate, LDA and chlorotriisopropoxytitanium at low temperature, preferably at −78° C. in a solvent such as an ether, e.g. diethyl ether or more preferably THF. Alternatively sulfinamide ester A3 can be produced from sulfinyl imine A2 by Reformatsky reaction of a bromoacetic ester derivative and zinc dust, optionally in the presence of copper(I) chloride, in a solvent such as an ether, e.g. diethyl ether or more preferably THF, at temperatures from 0 to 70° C., preferably at 23° C.

Sulfinamide ester A3 can be reduced to the alcohol A4 by the reduction of the ethylester with an alkali hydride, preferably lithium borohydride or lithium aluminium hydride in a solvent such as an ether, e.g. diethyl ether or more preferably THF.

Alkylation of the alcohol A4 to the nitrile A5 can be accomplished with a suitable mild base preferably silver(I) oxide in a solvent such as THF or $CH_2Cl_2$, more preferably $CH_2Cl_2$ in the presence of an alkylating catalyst such as tertra butyl ammonium iodide.

Hydrolysis of the chiral directing group in the nitrile A5 to give the amino nitrile A6 can be accomplished with a mineral acid, e.g. sulfuric acid or preferably hydrochloric acid in a solvent such as an ether, e.g. diethyl ether or more preferably 1,4-dioxane.

Aminooxazepine A7 can be prepared by the reaction of amino nitrile A6 and trimethyl aluminium in a solvent such as an xylene, preferably toluene.

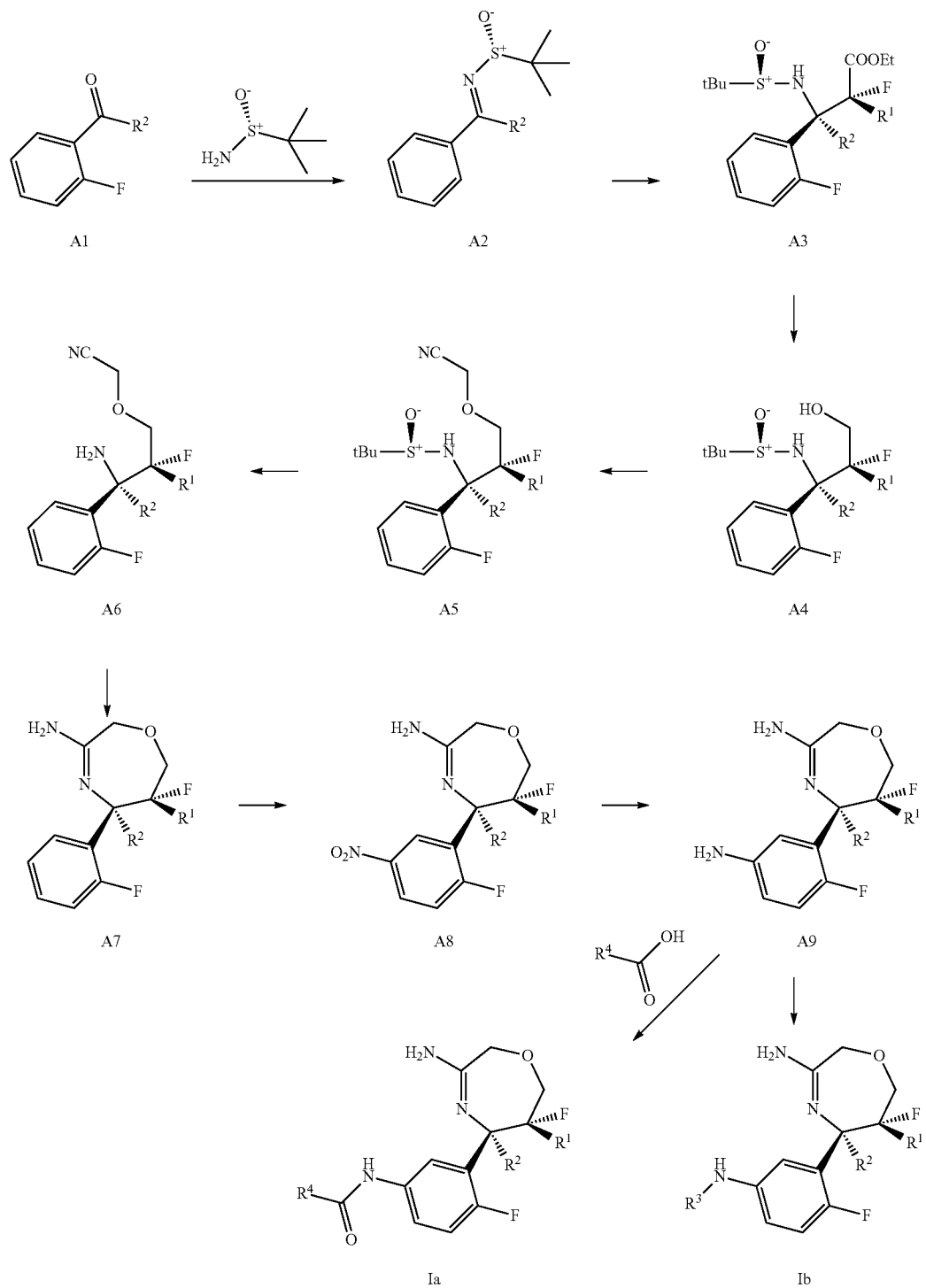

Scheme A

Introduction of the nitro group in A7 to give A8 was best performed according to the standard procedure involving sulfuric acid and nitric acid at low temperature, preferably at 0° C.

The reduction of the nitro group in aminooxazepine A8 to the aniline A9 can be accomplished by hydrogenation using a catalysts such as Pd/C in protic solvents, such as alcohols, perferrabyl ethanol or methanol.

Amide coupling of the aniline A9 and a carboxylic acid to give the amide Ia can be effected with a carbodiimide, e.g. DCC or EDCI in a solvent such as dichloromethane or in particular with a triazine derivative, 4-(4,6-dimethoxy-1,3,5-triazin-2-yl)-4-methyl-morpholiniumchloride in an alcohol in particular methanol.

Target amines Ib can be prepared via reductive amination of aniline A9 and a carbonyl compound performed with a borohydride reducing agent, e.g. sodium borohydride, preferable sodium triacetoxyborohydride and an weak acid, e.g. acetic acid in a solvent such as tetrahydrofuran or dichloromethane.

Compounds of formula I can form pharmaceutically acceptable salts. The term "pharmaceutically acceptable salts" refers to those salts which retain the biological effectiveness and properties of the free bases or free acids, which are not biologically or otherwise undesirable. Preferably, the pharmaceutically acceptable salts of the compounds of formula I are the acid addition salts with physiologically compatible mineral acids, such as hydrochloric acid, sulfuric acid, sulfurous acid or phosphoric acid; or with organic acids, such as methanesulfonic acid, ethanesulfonic acid, p-toluenesulfonic acid, formic acid, acetic acid, propionic acid, glycolic acid, pyruvic acid, oxylic acid, lactic acid, trifluoroacetic acid, citric acid, fumaric acid, maleic acid, malonic acid, tartaric acid, benzoic acid, cinnamic acid, mandelic acid, succinic acid or salicylic acid. In addition, pharmaceutically acceptable salts can be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particular pharmaceutically acceptable salts of compounds of formula I are the acid addition salts such as the hydrochloride salts, the formate salts or trifluoroacetate salts. Specific are the formate salts (salts of formic acid).

The corresponding pharmaceutically acceptable salts with acids can be obtained by standard methods known to the person skilled in the art, e.g. by dissolving the compound of formula I in a suitable solvent such as e.g. dioxan or THF and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation. Particular salts are hydrochloride, formate and trifluoroacetate.

Insofar as their preparation is not described in the examples, the compounds of formula I as well as all intermediate products can be prepared according to analogous methods or according to the methods set forth herein. Starting materials are commercially available, known in the art or can be prepared by methods known in the art or in analogy thereto.

It will be appreciated that the compounds of general formula I in this invention can be derivatized at functional groups to provide derivatives which are capable of conversion back to the parent compound in vivo.

Pharmacological Tests

The compounds of formula I and their pharmaceutically acceptable salts possess valuable pharmacological properties. Compounds of the present invention are associated with inhibition of BACE1 and/or BACE2 activity. The compounds were investigated in accordance with the tests given hereinafter.

Cellular Aβ-lowering Assay:

Human HEK293 cells which are stably transfected with a vector expressing a cDNA of the human APP wt gene (APP695) were used to assess the potency of the compounds in a cellular assay. The cells were seeded in 96-well microtiter plates in cell culture medium (Iscove, plus 10% (v/v) fetal bovine serum, glutamine, penicillin/streptomycin) to about 80% confluence and the compounds were added at a 10× concentration in 1/10 volume of medium without FCS containing 8% DMSO (final concentration of DMSO was kept at 0.8% v/v). After 18-20 hrs incubation at 37° C. and 5% $CO_2$ in a humidified incubator the culture supernatant was harvested for the determination of Aβ40 concentrations. 96 well ELISA plates (e.g., Nunc MaxiSorb) were coated with monoclonal antibody which specifically recognize the C-terminal end of Aβ40 (Brockhaus et al., NeuroReport 9, 1481-1486; 1998). After blocking of non-specific binding sites with e.g. 1% BSA and washing, the culture supernatants were added in suitable dilutions together with a horseradish peroxidase-coupled Aβ detection antibody (e.g., antibody 4G8, Senetek, Maryland Heights, Mo.) and incubated for 5 to 7 hrs. Subsequently the wells of the microtiter plate were washed extensively with Tris-buffered saline containing 0.05% Tween 20 and the assay was developed with tetramethylbenzidine/ $H_2O_2$ in citric acid buffer. After stopping the reaction with one volume 1 $NH_2SO_4$ the reaction was measured in an ELISA reader at 450 nm wavelength. The concentrations of Aβ in the culture supernatants were calculated from a standard curve obtained with known amounts of pure Aβ peptide.

Assay for BACE Inhibition by Measuring Cellular TMEM27 Cleavage:

The assay uses the principle of inhibition of human TMEM27 cleavage by endogenous cellular BACE2 in the Ins 1e rat cell line and shedding from the cell surface into the culture medium, followed by detection in an ELISA assay. Inhibition of BACE2 prevents the cleavage and shedding in a dose-dependent manner.

The stable cell line "INS-TMEM27" represents an INSle-derived cell line with inducible expression (using the TetOn system) of full-length hTMEM27 in a doxycycline-dependent manner. The cells are cultured throughout the experiment in RPMI1640+Glutamax (Invitrogen) Penicillin/Streptomycin, 10% Fetal bovine serum, 100 mM pyruvate, 5 mM beta-mercatptoethanol, 100 micrograms/ml G418 and 100 microgram/ml hygromycin and are grown inadherent culture at 37° C. in a standard $CO_2$ cell culture incubator.

INS-TMEM27 cells are seeded in 96-well plates. After 2 days in culture, BACE2 inhibitor is added in a range of concentrations as required by the assay and after a further two hours, doxycycline is added to a final concentration of 500 ng/ml. The cells are incubated for a further 46 hours and the supernatant harvested for detection of shed TMEM27.

An ELISA assay (using a pair of mouse anti-human-TMEM27 antibodies, raised against the extracellular domain of TMEM27) is used for detection of TMEM27 in the culture medium. An $EC_{50}$ for BACE2 inhibition is calculated using the ELISA readout for each inhibitor concentration with standard curve-fitting software such as XLFit for the Excel spreadsheet program.

The preferred compounds according to formula I have an inhibitory activity in the above assay ($IC_{50}$) preferably of 5 nM to 50 μM, more preferably of 5 nM to 1 μM.

For example, the following compounds showed the following $IC_{50}$ values in the assay described above:

| Example | Cellular assay TMEM27 $IC_{50}$ [μM] | Cellular assay Abeta40 $IC_{50}$ [μM] |
|---|---|---|
| 1 | 14.56998 | 0.35 |
| 2 | — | — |
| 3 | 5.73 | 0.01 |
| 4 | 0.66187 | 2.4 |
| 5 | 0.10322 | 0.01 |
| 6 | 0.31103 | 0.02 |
| 7 | 0.12292 | 0.025 |
| 8 | 0.837 | 0.07 |
| 9 | 0.02256 | 0.028 |

Pharmaceutical Compositions

The compounds of formula I and the pharmaceutically acceptable salts can be used as therapeutically active substances, e.g. in the form of pharmaceutical compositions. The pharmaceutical compositions can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula I and the pharmaceutically acceptable salts thereof can be processed with pharmaceutically inert, inorganic or organic carriers for the production of pharmaceutical compositions. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The invention also provides pharmaceutical compositions containing a compound of formula I or a pharmaceutically acceptable salt thereof and a therapeutically inert carrier as well as a process for their production, which comprises bringing one or more compounds of formula I and/or pharmaceutically acceptable salts thereof and, if desired, one or more other therapeutically valuable substances into a galenical administration form together with one or more therapeutically inert carriers.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day, especially from about 1 to 500 mg per day, of a compound of formula I or of the corresponding amount of a pharmaceutically acceptable salt thereof. Depending on severity of the disease and the precise pharmacokinetic profile of the compound, the daily dosage can be administered as single dose or in divided doses and, in addition, the upper limit can also be exceeded when this is found to be indicated.

The following examples illustrate the present invention without limiting it, but serve merely as representative thereof. Examples of compositions according to the invention are:

EXAMPLE A

Tablets of the following composition are manufactured in the usual manner

TABLE 1 possible tablet composition

| ingredient | mg/tablet | | | |
|---|---|---|---|---|
| | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure:
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

EXAMPLE B-1

Capsules of the following composition are manufactured:

TABLE 2 possible capsule ingredient composition

| ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure:
1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer, the talc is added thereto and mixed thoroughly. The mixture is filled by machine into suitable capsules, e.g. hard gelatin capsules.

EXAMPLE B-2

Soft Gelatin Capsules of the following composition are manufactured:

TABLE 3 possible soft gelatin capsule ingredient composition

| ingredient | mg/capsule |
| --- | --- |
| Compound of formula I | 5 |
| Yellow wax | 8 |
| Hydrogenated Soya bean oil | 8 |
| Partially hydrogenated plant oils | 34 |
| Soya bean oil | 110 |
| Total | 165 |

TABLE 4 possible soft gelatin capsule composition

| ingredient | mg/capsule |
| --- | --- |
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

The compound of formula I is dissolved in a warm melting of the other ingredients and the mixture is filled into soft gelatin capsules of appropriate size. The filled soft gelatin capsules are treated according to the usual procedures.

EXAMPLE C

Suppositories of the following composition are manufactured:

TABLE 5 possible suppository composition

| ingredient | mg/supp. |
| --- | --- |
| Compound of formula I | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool, the suppositories are then removed from the moulds and packed individually in wax paper or metal foil.

EXAMPLE D

Injection solutions of the following composition are manufactured:

TABLE 6 possible injection solution composition

| ingredient | mg/injection solution. |
| --- | --- |
| Compound of formula I | 3 |
| Polyethylene Glycol 400 | 150 |
| acetic acid | q.s. ad pH 5.0 |
| water for injection solutions | ad 1.0 ml |

Manufacturing Procedure

The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

EXAMPLE E

Sachets of the following composition are manufactured:

TABLE 7 possible sachet composition

| ingredient | mg/sachet |
| --- | --- |
| Compound of formula I | 50 |
| Lactose, fine powder | 1015 |
| Microcrystalline cellulose (AVICEL PH 102) | 1400 |
| Sodium carboxymethyl cellulose | 14 |
| Polyvinylpyrrolidone K 30 | 10 |
| Magnesium stearate | 10 |
| Flavoring additives | 1 |
| Total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

EXAMPLES

General:

MS: Mass spectra (MS) were measured either with ion spray positive or negative (ISP or ISN) method on a Perkin-Elmer SCIEX API 300 or with electron impact method (EI, 70 eV) on a Finnigan MAT SSQ 7000 spectrometer.

Abbreviations:

DCC=N,N'-diisopropyl-carbodiimide, DCE=1,2-dichloroethane, DCM=dichloromethane, DIEA=diisopropylethylamine, DMAc=dimethylacetamide, DMAP=4-dimethylaminopyridine, DMF=N,N-dimethylformamide, DMSO=dimethyl sulfoxide, EDCI=N-(3-dimethylaminopropyl)-N'-ethyl-carbodiimide hydrochloride, HATU=1-[bis(dimethylamino)methylene]-1H-1,2,3-triazolo[4,5-b]pyridinium-3-oxide hexafluorophosphate, HCl=hydrogen chloride, HPLC=high performance liquid chromatography, LDA=lithium diisopropylamide, MS=mass spectrum, NMR=nuclear magnetic resonance, TEA=triethylamine, TBME=tert-butyl methyl ether, and THF=tetrahydrofuran.

The following examples are provided for illustration of the invention. They should not be considered as limiting the scope of the invention, but merely as being representative thereof.

Synthesis of the Intermediate 1-(2-fluoro-5-nitro-phenyl)-propan-1-one A1A

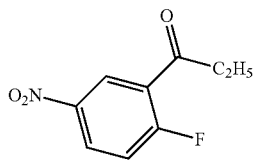 [SMILES: CCC(=O)c1cc([N+](=O)[O-])ccc1F]

To a solution of the 1-(2-fluoro-phenyl)-propan-1-one (99 mmol) in concentrated sulfuric acid (80 ml) cooled down to −30° C. was added slowly fuming nitric acid (8 ml) over 20 min and the solution was stirred at −30° C. for 15 min. The mixture was slowly poured into a stirred mixture of 200 ml of water and 400 g ice. The aqueous phase was extracted with ethyl acetate, the organic layer was extracted again with water and aqueous NaHCO$_3$ 1M. The organic layer was dried over Na$_2$SO$_4$, evaporated and the residue was purified by chromatography on silica using a mixture of heptane and ethylacetate as eluent to afford the pure nitro intermediate J. MS (ISP): m/z=198.1 [M+H]+.

Synthesis of the Intermediate Sulfinyl Imines A2
General Procedure:

To a solution of the (R)-(+)-tert-butylsulfinamide (66 mmol) in THF (350 ml) was added subsequently the ketone A1 (72.6 mmol) and titanium(IV)ethoxide (132 mmol) and the solution was stirred at reflux temperature for 5 h. The mixture was cooled to 22° C., treated with brine (400 ml), the suspension was stirred for 10 min and filtered over dicalite. The layers were separated, the aqueous layer was extracted with ethyl acetate, the combined organic layers were washed with water, dried and concentrated in vacuo. The residue was purified by chromatography on silica using cylohexane/ethyl acetate to give the pure sulfinyl imine A2.

Intermediate A2A

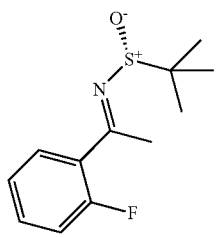 [SMILES: C/C(=N\[S@+]([O-])C(C)(C)C)c1ccccc1F]

Starting from 1-(2-fluorophenyl)-ethanone, the product (R)-2-methyl-propane-2-sulfinic acid [1-(2-fluorophenyl)-(E)-ethylidene]-amide was obtained as pale brown oil. MS (ISP): m/z=242.3 [M+H]$^+$.

Intermediate A2B

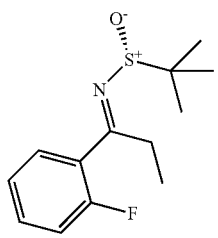 [SMILES: CC/C(=N\[S@+]([O-])C(C)(C)C)c1ccccc1F]

Starting from 1-(2-fluoro-phenyl)-propan-1-one, the product 2-methyl-propane-2-sulfinic acid [1-(2-fluoro-phenyl)-prop-(E)-ylidene]-amide was obtained as pale yellow oil. MS: m/z=256.2 [M+H]$^+$.

Synthesis of the Intermediate Sulfinamide Esters A3
General Procedure:

In a dry apparatus a suspension of freshly activated zinc powder (1.63 g, 24.9 mmol) in dry THF (70 ml) was heated under inert atmosphere to reflux. A solution of the sulfinyl imine A2 (24.9 mmol) and the bromo-acetate (24.9 mmol) in dry THF (15 ml) was added dropwise over a period of 15 min and the suspension was heated to reflux for 5 h. The cooled mixture was partitioned between aqueous saturated NH$_4$Cl and ethyl acetate, the organic layer was dried and evaporated. The crude material was purified by flash chromatography using heptane/ethyl acetate to give the sulfinamide ester A3.

Intermediates A3A and A3B

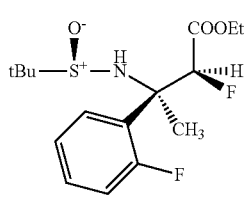

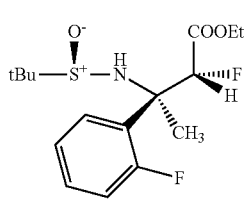

Starting from (R)-2-methyl-propane-2-sulfinic acid [1-(2-fluorophenyl)-(E)-ethylidene]-amide and ethyl 2-bromo-2-fluoroacetate, the faster eluting minor isomer (2S,3R)-ethyl 3-((R)-1,1-dimethylethylsulfinamido)-2-fluoro-3-(2-fluorophenyl)butano ate (intermediate A3A) was obtained as a dark brown oil. MS (ISP): m/z=348.2 [M+H]$^+$.

The second fraction contained the slower eluting major isomer (2R,3R)-ethyl 3-((R)-1,1-dimethylethylsulfinamido)-2-fluoro-3-(2-fluorophenyl)butanoate (intermediate A3B) as a brown oil. MS (ISP): m/z=348.2 [M+H]$^+$.

Intermediates A3C

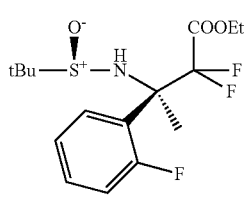 [SMILES: CCOC(=O)C(F)(F)[C@](C)(N[S@@+]([O-])C(C)(C)C)c1ccccc1F]

Starting from (R)-2-methyl-propane-2-sulfinic acid [1-(2-fluorophenyl)-(E)-ethylidene]-amide the product (R)-2,2-difluoro-3-(2-fluoro-phenyl)-3-(R)-2-methyl-propane-2-sulfinylamino)-butyric acid ethyl ester was obtained as a pale yellow oil. MS: m/z=366.1 [M+H]$^+$.

Intermediates A3D

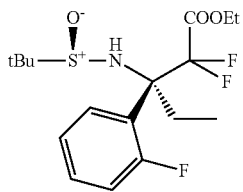 [SMILES: CCOC(=O)C(F)(F)[C@](CC)(N[S@@+]([O-])C(C)(C)C)c1ccccc1F]

Starting from 2-methyl-propane-2-sulfinic acid [1-(2-fluoro-phenyl)-prop-(E)-ylidene]-amide the product (R)-2,2-difluoro-3-(2-fluoro-phenyl)-3-(R)-2-methyl-propane-2-sulfinylamino)-pentanoic acid ethyl ester was obtained as a colorless oil. MS: m/z=380.2 [M+H]$^+$.

Synthesis of the Intermediate Sulfinamide Alcohols A4

General Procedure:

A solution of the sulfinamide ester A3 (12.7 mmol) in dry THF (50 ml) was treated at 0° C. with lithium borohydride (25.3 mmol) and stirring was continued at 0° C. for 4 h. The reaction mixture was quenched by addition of acetic acid (2 ml) and water (50 ml), extracted with ethyl acetate and the organic layer was dried and evaporated. The residue was purified by chromatography on silica using a mixture of n-heptane and ethyl acetate to give the pure intermediate sulfinamide alcohol A4.

Intermediate A4A

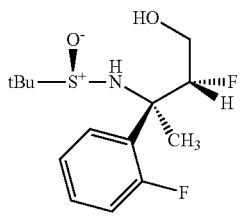 [SMILES: CC(C)(C)[S@+]([O-])N[C@](C)(c1ccccc1F)[C@@H](F)CO]

Starting from (2R,3R)-ethyl 3-((R)-1,1-dimethylethylsulfinamido)-2-fluoro-3-(2-fluorophenyl)butanoate, the product (R)-2-methyl-propane-2-sulfinic acid [(1R,2R)-2-fluoro-1-(2-fluoro-phenyl)-3-hydroxy-1-methyl-propyl]-amide was obtained as pale red crystals. MS (ISP): m/z=306.1 [M+H]$^+$.

Intermediate A4B

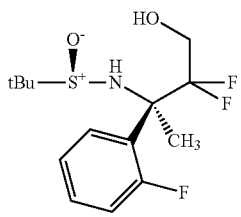 [SMILES: CC(C)(C)[S@+]([O-])N[C@](C)(c1ccccc1F)C(F)(F)CO]

Starting from (R)-2,2-difluoro-3-(2-fluoro-phenyl)-3-(R)-2-methyl-propane-2-sulfinylamino)-butyric acid ethyl ester, the product 2-methyl-propane-2-sulfinic acid [(R)-2,2-difluoro-1-(2-fluoro-phenyl)-3-hydroxy-1-methyl-propyl]-amide was obtained as a white solid. MS (ISP): m/z=324.2 [M+H]$^+$.

Intermediate A4C

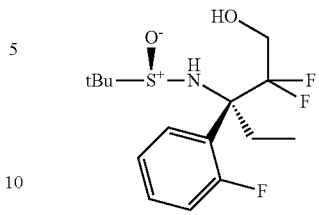

Starting from (R)-2,2-difluoro-3-(2-fluoro-phenyl)-3-(R)-2-methyl-propane-2-sulfinylamino)-pentanoic acid ethyl ester, the product 2-methyl-propane-2-sulfinic acid [(R)-1-ethyl-2,2-difluoro-1-(2-fluoro-phenyl)-3-hydroxy-propyl]-amide was obtained as a white solid. MS (ISP): m/z=338.1 [M+H]$^+$.

Synthesis of the Intermediate Sulfinamide Nitrile A5

General Procedure

To a solution of the sulfinamide alcohol A4 (4.1 mmol) in dichloromethane (23 ml) was subsequently added at 22° C. 2-bromoacetonitrile (6.2 mmol), silver(I) oxide (1.9 g) and tetrabutylammonium iodide (0.30 g) and stirring was continued for 2 h. The suspension was filtered, the filtrate was washed with aqueous saturated NaHCO$_3$ solution, the organic layer was dried and evaporated to give the crude sulfinamide nitrile A5 which was used without further purification.

Intermediate A5A

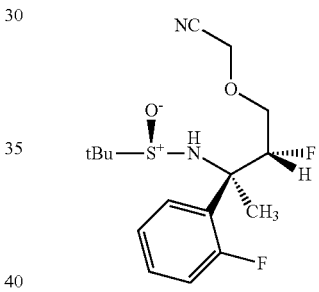

Starting from (R)-2-methyl-propane-2-sulfinic acid [(1R,2R)-2-fluoro-1-(2-fluoro-phenyl)-3-hydroxy-1-methyl-propyl]-amide, the product (R)—N-((2R,3R)-4-(cyanomethoxy)-3-fluoro-2-(2-fluorophenyl)butan-2-yl)-2-methylpropane-2-sulfinamide was obtained as a pale yellow oil. MS (ISP): m/z=345.2 [M+H]$^+$.

Intermediate A5B

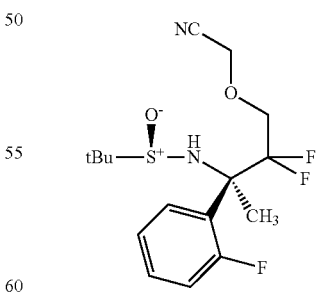

Starting from 2-methyl-propane-2-sulfinic acid [(R)-2,2-difluoro-1-(2-fluoro-phenyl)-3-hydroxy-1-methyl-propyl]-amide, the product 2-methyl-propane-2-sulfinic acid [(R)-3-cyanomethoxy-2,2-difluoro-1-(2-fluoro-phenyl)-1-methyl-propyl]-amide was obtained as a pale yellow oil. MS (ISP): m/z=363.2 [M+H]$^+$.

Intermediate A5C

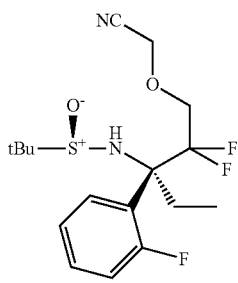 [SMILES: CC[C@@](N[S@@+]([O-])C(C)(C)C)(c1ccccc1F)C(F)(F)COCC#N]

Starting from 2-methyl-propane-2-sulfinic acid [(R)-1-ethyl-2,2-difluoro-1-(2-fluoro-phenyl)-3-hydroxy-propyl]-amide, the product 2-methyl-propane-2-sulfinic acid [(R)-3-cyanomethoxy-1-ethyl-2,2-difluoro-1-(2-fluoro-phenyl)-propyl]-amide was obtained as a pale yellow oil. MS (ISP): m/z=377.3 [M+H]⁺.

Synthesis of the Intermediate Amino Nitrile A6

General Procedure

A solution of the sulfinamide nitrile A5 (4.25 mmol) in 1,4-dioxane (20 ml) was treated with a solution of HCl in 1,4-dioxane (4 M, 5.3 ml) and stirring was continued at 22° C. for 1 h. The mixture was diluted with ethyl acetate, washed with saturated aqueous Na₂CO₃ solution, the organic layer was dried and evaporated. The crude material was purified on silica using n-heptane/ethyl acetate to give the pure amino nitrile A6.

Intermediate A6A

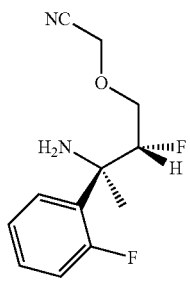 [SMILES: C[C@@](N)(c1ccccc1F)[C@@H](F)COCC#N]

Starting from (R)—N42R,3R)-4-(cyanomethoxy)-3-fluoro-2-(2-fluorophenyl)butan-2-yl)-2-methylpropane-2-sulfinamide, the product 2-((2R,3R)-3-amino-2-fluoro-3-(2-fluorophenyl)butoxy)acetonitrile was obtained as a pale yellow oil. MS (ISP): m/z=241.1 [M+H]⁺.

Intermediate A6B

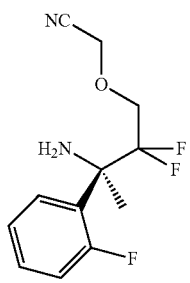 [SMILES: C[C@@](N)(c1ccccc1F)C(F)(F)COCC#N]

Starting from 2-methyl-propane-2-sulfinic acid [(R)-3-cyanomethoxy-2,2-difluoro-1-(2-fluoro-phenyl)-1-methyl-propyl]-amide, the product [(R)-3-amino-2,2-difluoro-3-(2-fluoro-phenyl)-butoxy]-acetonitrile was obtained as a pale yellow oil. MS (ISP): m/z=259.1 [M+H]⁺.

Intermediates A6C

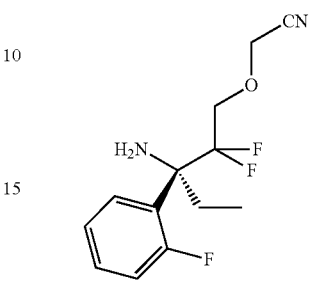

Starting from 2-methyl-propane-2-sulfinic acid [(R)-3-cyanomethoxy-1-ethyl-2,2-difluoro-1-(2-fluoro-phenyl)-propyl]-amide, the product [(R)-3-amino-2,2-difluoro-3-(2-fluoro-phenyl)-pentyloxy]-acetonitrile was obtained as a pale yellow oil. MS: m/z=273.1 [M+H]⁺.

Synthesis of the Intermediate 1,4-oxazepine A7

General Procedure:

To a solution of the amino nitrile A6 (2.20 mmol) in toluene (38 ml) was added at 22° C. a solution of AlMe₃ in toluene (2 M, 1.2 ml) and the mixture was heated to 80° C. for 1 h. The mixture was cooled to 0° C., diluted with saturated aqueous Na₂CO₃ and the aqueous layer was extracted with ethyl acetate. The combined organic layers were dried, evaporated and the residue purified by chromatography on NH₂-silica using n-heptane/ethyl acetate to give the pure 1,4-oxazepine A7.

Intermediate A7A

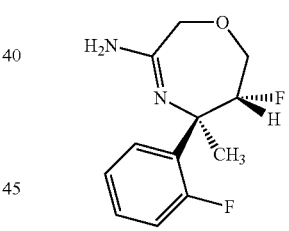

Starting from 2-((2R,3R)-3-amino-2-fluoro-3-(2-fluorophenyl)butoxy)acetonitrile, the product (5R,6R)-6-fluoro-5-(2-fluorophenyl)-5-methyl-2,5,6,7-tetrahydro-1,4-oxazepin-3-amine was obtained as a pale yellow solid. MS (ISP): m/z=241.2 [M+H]⁺.

Intermediate A7B

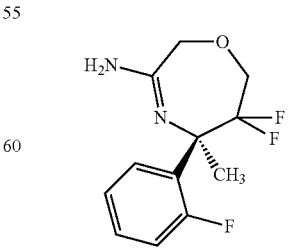

Starting from [(R)-3-amino-2,2-difluoro-3-(2-fluoro-phenyl)-butoxy]-acetonitrile, the product (R)-6,6-difluoro-5-(2- fluoro-phenyl)-5-methyl-2,5,6,7-tetrahydro-[1,4]oxazepin-3-ylamine was obtained as a white solid. MS (ISP): m/z=259.1 [M+H]⁺.

Intermediates A7C

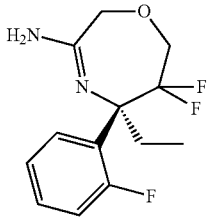 [SMILES: CC[C@]1(c2ccccc2F)N=C(N)COCC1(F)F]

Starting from [(R)-3-amino-2,2-difluoro-3-(2-fluoro-phenyl)-pentyloxy]-acetonitrile, the product (R)-5-ethyl-6,6-difluoro-5-(2-fluoro-phenyl)-2,5,6,7-tetrahydro-[1,4]oxazepin-3-ylamine was obtained as a brown oil. MS: m/z=273.1 [M+H]⁺.

Intermediate Nitrobenzene A8
General Procedure:

To a solution of the intermediate 1,4-oxazepine A7 (1.2 mmol) in sulfuric acid (5.0 ml) was added at 0° C. red fuming nitric acid (1.9 mmol) over a period of 20 min and stirring was continued for 30 min. The solution was dropped slowly into ice/water (60 ml), the pH was adjusted to 9 by addition of aqueous 4 N NaOH and extracted with ethyl acetate. The organic layer was dried, evaporated and the residue purified by chromatography on silca-NH₂ using n-heptane/ethyl acetate to give the nitrobenzene A8.

Intermediate A8A

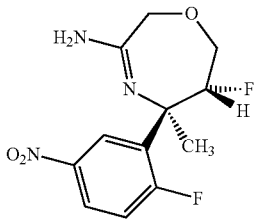

Starting from (5R,6R)-6-fluoro-5-(2-fluorophenyl)-5-methyl-2,5,6,7-tetrahydro-1,4-oxazepin-3-amine the product (5R,6R)-6-fluoro-5-(2-fluoro-5-nitro-phenyl)-5-methyl-2,5,6,7-tetrahydro-[1,4]oxazepin-3-ylamine was obtained as a pale yellow solid. MS (ISP): m/z=286.2 [M+H]⁺.

Intermediate A8B

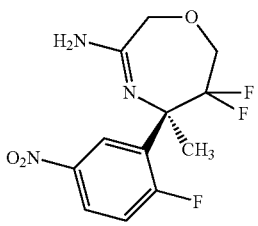 [SMILES: C[C@]1(c2cc([N+](=O)[O-])ccc2F)N=C(N)COCC1(F)F]

Starting from (R)-6,6-difluoro-5-(2-fluoro-phenyl)-5-methyl-2,5,6,7-tetrahydro-[1,4]oxazepin-3-ylamine the product (R)-6,6-difluoro-5-(2-fluoro-5-nitro-phenyl)-5-methyl-2,5,6,7-tetrahydro-[1,4]oxazepin-3-ylamine was obtained as a white solid. MS (ISP): m/z=304.1 [M+H]⁺.

Intermediate A8C

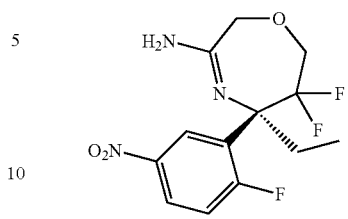

Starting from (R)-5-ethyl-6,6-difluoro-5-(2-fluoro-phenyl)-2,5,6,7-tetrahydro-[1,4]oxazepin-3-ylamine the product (R)-5-ethyl-6,6-difluoro-5-(2-fluoro-5-nitro-phenyl)-2,5,6,7-tetrahydro-[1,4]oxazepin-3-ylamine was obtained as a pale yellow solid. MS: m/z=318.1 [M+H]⁺.

Synthesis of the Intermediate Aniline A9
General Procedure:

A suspension of the intermediate nitrobenzene A8 (1.0 mmol) in ethanol (9 ml) and Pd/C (10%, 100 mg) was hydrogenated at 22° C. and atmospheric pressure for 2 h. The suspension was filtered and the residue evaporated to give the crude aniline A10 which was used without further purification.

Intermediate A9A

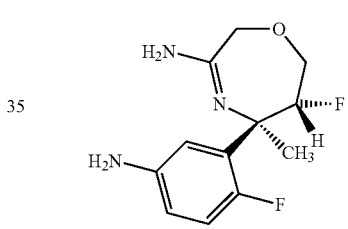

Starting from (5R,6R)-6-fluoro-5-(2-fluoro-5-nitro-phenyl)-5-methyl-2,5,6,7-tetrahydro-[1,4]oxazepin-3-ylamine the product (5R,6R)-5-(5-amino-2-fluorophenyl)-6-fluoro-5-methyl-2,5,6,7-tetrahydro-1,4-oxazepin-3-amine was obtained as a pale yellow solid. MS (ISP): m/z=256.3 [M+H]⁺.

Intermediate A9B

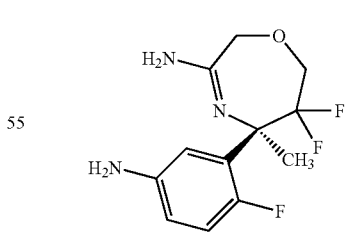

Starting from (R)-6,6-difluoro-5-(2-fluoro-5-nitro-phenyl)-5-methyl-2,5,6,7-tetrahydro-[1,4]oxazepin-3-ylamine the product (R)-5-(5-amino-2-fluoro-phenyl)-6,6-difluoro-5-methyl-2,5,6,7-tetrahydro-[1,4]oxazepin-3-ylamine was obtained as a white solid. MS (ISP): m/z=274.1 [M+H]⁺.

Intermediate A9C

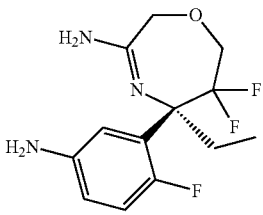 [SMILES: CC[C@]1(c2cc([N+](=O)[O-])ccc2F)N=C(N)COCC1(F)F]

Starting from (R)-5-ethyl-6,6-difluoro-5-(2-fluoro-5-nitro-phenyl)-2,5,6,7-tetrahydro-[1,4]oxazepin-3-ylamine the product (R)-5-(5-amino-2-fluoro-phenyl)-5-ethyl-6,6-difluoro-2,5,6,7-tetrahydro-[1,4]oxazepin-3-ylamine was obtained as a pale yellow solid. MS: m/z=288.1 [M+H]$^+$.

Synthesis of the Amides Ia from the Anilines A9
General Procedure:

To a solution of the acid (0.16 mmol) in MeOH (1 ml) was added at 22° C. 4-(4,6-dimethoxy-1,3,5-triazin-2-yl)-4-methyl-morpholiniumchloride (0.19 mmol) and stirring was continued at 0° C. for 30 min. To the mixture was added a solution of the aniline A9 (0.15 mmol) in MeOH (2 ml) and stirring was continued at 0° C. for 2 h. The mixture was diluted with saturated aqueous Na$_2$CO$_3$, the MeOH was evaporated and the aqueous solution was extracted with ethyl acetate. The organic layer was dried, evaporated and the residue was purified on preparative HPLC RP18 column using a gradient of water/HCOOH (99.9:0.1)->MeOH to give the formiate salt or a gradient of water/NEt$_3$ (99.9:0.1)->CH$_3$CN to give the free base of the amide Ia.

Synthesis of the Amines Ib from the Anilines A9 by Reductive Amination
General Procedure:

To a solution of the aniline A9 (0.1 mmol) in dichloromethane (0.7 ml) was subsequently added at 22° C. the carbonyl compound (0.11 mmol), acetic acid (0.2 mmol) and sodium triacetoxyborohydride (0.14 mmol) and stirring of the mixture was continued for 18 h. The mixture was diluted with water (1 ml), the organic layer was washed with saturated aqueous NaHCO$_3$, dried and evaporated. The residue was purified by chromatography on a silica-NH$_2$ column using dichloromethane to give the amines Ib

EXAMPLE 1

(R)—N2-(3-(3-Amino-6,6-difluoro-5-methyl-2,5,6,7-tetrahydro-1,4-oxazepin-5-yl)-4-fluorophenyl)-3-fluoropyridine-2,5-dicarboxamide formate

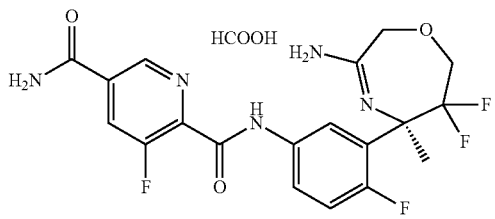 [SMILES: C[C@]1(c2cc(NC(=O)c3ncc(C(N)=O)cc3F)ccc2F)N=C(N)COCC1(F)F ; "HCOOH"]

The coupling of (R)-5-(5-amino-2-fluorophenyl)-6,6-difluoro-5-methyl-2,5,6,7-tetrahydro-1,4-oxazepin-3-amine (intermediate A9B) and 5-carbamoyl-3-fluoro-pyridine-2-carboxylic acid (prepared according to Hori, A. et al., Int. Patent Application Publ. No. WO2009151098) yielded the title compound as an off-white amorphous material. MS (ISP): m/z=440.2 [M+H]$^+$.

EXAMPLE 2

(R)—N-(3-(3-Amino-6,6-difluoro-5-methyl-2,5,6,7-tetrahydro-1,4-oxazepin-5-yl)-4-fluorophenyl)-6-(cyclopropylmethoxy)picolinamide formate

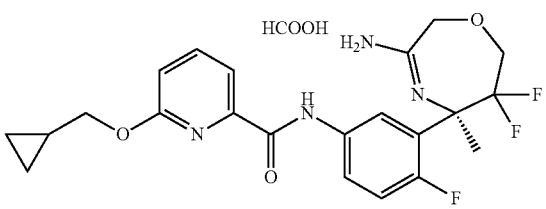 [SMILES: C[C@]1(c2cc(NC(=O)c3cccc(OCC4CC4)n3)ccc2F)N=C(N)COCC1(F)F ; "HCOOH"]

The coupling of (R)-5-(5-amino-2-fluorophenyl)-6,6-difluoro-5-methyl-2,5,6,7-tetrahydro-1,4-oxazepin-3-amine (intermediate A9B) and 6-cyclopropylmethoxy-pyridine-2-carboxylic acid yielded the title compound as an off-white amorphous material. MS (ISP): m/z=449.2 [M+H]$^+$.

The 6-cyclopropylmethoxy-pyridine-2-carboxylic acid was obtained as follows:

A solution of 6-chloro-pyridine-2-carboxylic acid (9.46 mmol) in dry dimethylsulfoxide (5 ml) was treated with cyclopropyl-methanol (14.1 mmol) followed by powdered potassium hydroxide (37.8 mmol). The reaction mixture was then irradiated in a microwave oven at 100° C. for 90 minutes. For the workup, the reaction mixture was quenched with aqueous citric acid (10%, pH 4-5), then extracted with ethyl acetate (5×30 ml), followed by extraction with a mixture of methanol and dichloromethane (20%; 5×100 ml). The combined organic layers were washed with brine (200 ml), dried and evaporated at reduced pressure. Lyophilization of the residue yielded the 6-chloro-pyridine-2-carboxylic acid as a brown solid (48% of theory) MS (ISP): m/z=195.0 [M+H]$^+$.

EXAMPLE 3

(R)—N-(3-(3-Amino-6,6-difluoro-5-methyl-2,5,6,7-tetrahydro-1,4-oxazepin-5-yl)-4-fluorophenyl)-5-(thiazol-2-yl)picolinamide formate

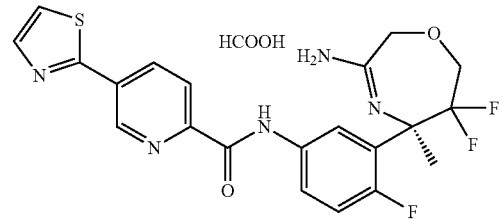 [SMILES: C[C@]1(c2cc(NC(=O)c3ccc(-c4nccs4)cn3)ccc2F)N=C(N)COCC1(F)F ; "HCOOH"]

The coupling of (R)-5-(5-amino-2-fluorophenyl)-6,6-difluoro-5-methyl-2,5,6,7-tetrahydro-1,4-oxazepin-3-amine (intermediate A9B) and 5-thiazol-2-yl-pyridine-2-carboxylic acid (prepared according to Suzuki, Y. et al., Int. Patent Application Publ. No. WO2009091016) yielded the title compound as an off-white amorphous material. MS (ISP): m/z=462.2 [M+H]$^+$.

EXAMPLE 4

(R)—N-(3-(3-Amino-5-ethyl-6,6-difluoro-2,5,6,7-tetrahydro-1,4-oxazepin-5-yl)-4-fluorophenyl)-5-cyclopropyloxazole-4-carboxamide

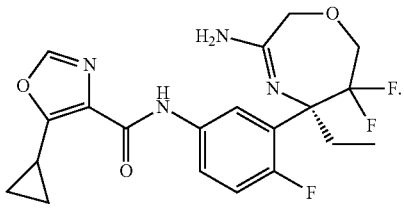 [SMILES: CC[C@]1(c2cc(NC(=O)c3ncoc3C3CC3)ccc2F)N=C(N)COCC1(F)F]

The coupling of (R)-5-(5-amino-2-fluoro-phenyl)-5-ethyl-6,6-difluoro-2,5,6,7-tetrahydro-[1,4]oxazepin-3-ylamine (intermediate A9C) and 5-cyclopropyl-oxazole-4-carboxylic acid yielded the title compound as a white solid. MS: m/z=423.2 [M+H]$^+$.

EXAMPLE 5

(R)—N-(3-(3-Amino-6,6-difluoro-5-methyl-2,5,6,7-tetrahydro-1,4-oxazepin-5-yl)-4-fluorophenyl)-5-(methylthio)pyrazine-2-carboxamide formate

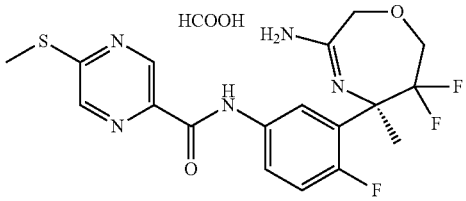 [SMILES: CSc1cnc(C(=O)Nc2ccc(F)c([C@@]3(C)N=C(N)COCC3(F)F)c2)cn1 ; "HCOOH"]

The coupling of (R)-5-(5-amino-2-fluorophenyl)-6,6-difluoro-5-methyl-2,5,6,7-tetrahydro-1,4-oxazepin-3-amine (intermediate A9B) and 5-methylsulfanyl-pyrazine-2-carboxylic acid (prepared according to Suzuki, Y. et al., Int. Patent Application Publ. No. WO2009091016) yielded the title compound as an off-white solid. MS (ISP): m/z=426.1 [M+H]$^+$.

EXAMPLE 6

(R)—N-(3-(3-Amino-6,6-difluoro-5-methyl-2,5,6,7-tetrahydro-1,4-oxazepin-5-yl)-4-fluorophenyl)-5-(cyclopropylethynyl)picolinamide formate

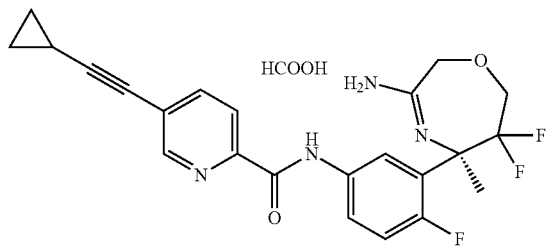 [SMILES: C[C@]1(c2cc(NC(=O)c3ccc(C#CC4CC4)cn3)ccc2F)N=C(N)COCC1(F)F ; "HCOOH"]

The coupling of (R)-5-(5-amino-2-fluorophenyl)-6,6-difluoro-5-methyl-2,5,6,7-tetrahydro-1,4-oxazepin-3-amine (intermediate A9B) and 5-cyclopropylethynyl-pyridine-2-carboxylic acid (prepared according to Suzuki, Y. et al., Int. Patent Application Publ. No. WO2009091016) yielded the title compound as an off-white solid. MS (ISP): m/z=443.3 [M+H]$^+$.

EXAMPLE 7

(R)—N-(3-(3-Amino-6,6-difluoro-5-methyl-2,5,6,7-tetrahydro-1,4-oxazepin-5-yl)-4-fluorophenyl)-5-cyclopropylpicolinamide formate

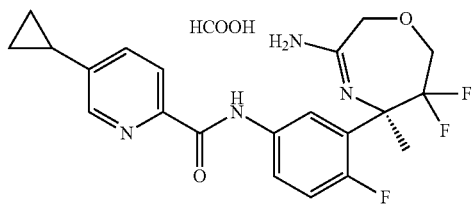 [SMILES: C[C@]1(c2cc(NC(=O)c3ccc(C4CC4)cn3)ccc2F)N=C(N)COCC1(F)F ; "HCOOH"]

The coupling of (R)-5-(5-amino-2-fluorophenyl)-6,6-difluoro-5-methyl-2,5,6,7-tetrahydro-1,4-oxazepin-3-amine (intermediate A9B) and 5-cyclopropyl-pyridine-2-carboxylic acid (prepared according to Suzuki, Y. et al., Int. Patent Application Publ. No. WO2009091016) yielded the title compound as an amorphous light yellow material. MS (ISP): m/z=419.2 [M+H]+.

EXAMPLE 8

(R)—N-(3-(3-Amino-6,6-difluoro-5-methyl-2,5,6,7-tetrahydro-1,4-oxazepin-5-yl)-4-fluorophenyl)-5-(3-methoxyprop-1-ynyl)picolinamide formate

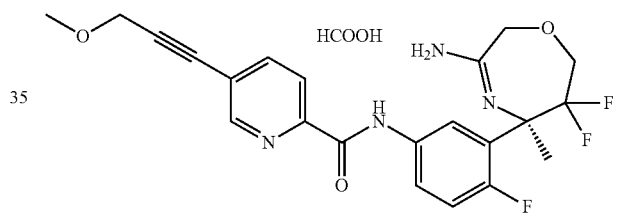

The coupling of (R)-5-(5-amino-2-fluorophenyl)-6,6-difluoro-5-methyl-2,5,6,7-tetrahydro-1,4-oxazepin-3-amine (intermediate A9B) and 5-(3-methoxy-prop-1-ynyl)-pyridine-2-carboxylic acid (prepared according to Suzuki, Y. et al., Int. Patent Application Publ. No. WO2009091016) yielded the title compound as a white solid. MS (ISP): m/z=410.2 [M+H]$^+$.

EXAMPLE 9

(5R,6R)-5-(5-(Cyclopropylmethylamino)-2-fluorophenyl)-6-fluoro-5-methyl-2,5,6,7-tetrahydro-1,4-oxazepin-3-amine

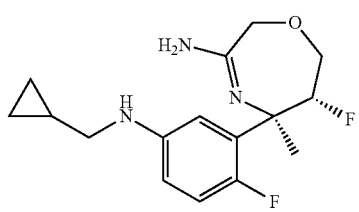 [SMILES: C[C@]1(c2cc(NCC3CC3)ccc2F)N=C(N)COC[C@@H]1F]

The reductive amination of (5R,6R)-5-(5-amino-2-fluorophenyl)-6-fluoro-5-methyl-2,5,6,7-tetrahydro-1,4-oxazepin-3-amine (intermediate A9A) and cyclopropanecarbaldehyde yielded the title compound as a colorless solid. MS: m/z=310.4 [M+H]$^+$.

The invention claimed is:
1. A compound of the formula I:

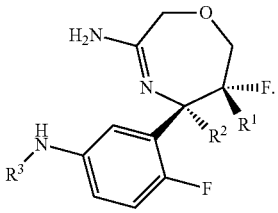

wherein
$R^1$ is H or F;
$R^2$ is $C_{1-7}$-alkyl; and
$R^3$ is $R^5$ and
$R^5$ is $C_{3-7}$-cycloalkyl-$C_{1-7}$-alkyl-;
or a pharmaceutically acceptable salt thereof.
2. The compound of claim 1, wherein $R^1$ is F.
3. The compound of claim 1, wherein $R^1$ is H.
4. The compound of claim 1, wherein $R^2$ is Me.
5. The compound of claim 1, wherein $R^2$ is Et.
6. The compound of claim 1, wherein $R^3$ is cyclopropyl-$CH_2$—.
7. The compound of claim 1, wherein said compound is (5R,6R)-5-[5-(Cyclopropylmethyl-amino)-2-fluoro-phenyl]-6-fluoro-5-methyl-2,5,6,7-tetrahydro-[1,4]oxazepin-3-ylamine.
8. A pharmaceutical composition comprising a therapeutically effective amount of a compound of formula I:

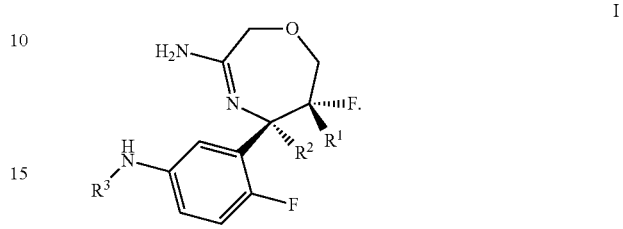

wherein
$R^1$ is H or F;
$R^2$ is $C_{1-7}$-alkyl; and
$R^3$ is $R^5$
$R^5$ is $C_{3-7}$-cycloalkyl-$C_{1-7}$-alkyl-;
or a pharmaceutically acceptable salt thereof and a pharmaceutically acceptable excipient.

* * * * *